United States Patent [19]

Singer, Jr.

[11] Patent Number: 5,376,532
[45] Date of Patent: Dec. 27, 1994

[54] METHODS FOR EVALUATING RISK OF DEVELOPING PERIODONTITIS

[75] Inventor: Robert E. Singer, Jr., Fairfield, Ohio

[73] Assignee: The Procter & Gamble Company, Cincinnati, Ohio

[21] Appl. No.: 947,657

[22] Filed: Sep. 18, 1992

[51] Int. Cl.$^5$ ............... G01N 33/52; G01N 33/53; G01N 33/569; G01N 33/573
[52] U.S. Cl. ............... 435/7.24; 435/7.32; 435/7.4; 435/967; 436/513
[58] Field of Search ............ 435/7.24, 7.32, 7.4, 435/967, 975, 973; 436/513

[56] References Cited

PUBLICATIONS

Cox et al, J. Periodont. Res., 25:164–171 (1990).
Cimasoni et al, Periodontology Today. Int. Congr., Zürich, pp. 260–268 (Karger, Basel, 1988).
Curtis et al, J. Clin. Periodont., 16:1–11 (1989).
Aarli, J. A., "Phenytoin–Induced Depression of Salivary IgA and Gingival Hyperplasia," Epilepsia, vol. 17, No. 3, pp. 283–291 (Sep. 1976).
Camling, E. & B. Kohler, "Infection With the Bacterium Streptococcus mutans and Salivary IgA Antibodies in Mothers and Their Children," Archs Oral Biol., vol. 32, No. 11, pp. 817–823 (month unknown 1987).
Challacombe, S. J., M. W. Russell, J. E. Hawkes, L. A. Bergmeier & T. Lehner, "Passage of immunoglobulins from plasma to the oral cavity in rhesus monkeys," Immunology, vol. 35, No. 6, pp. 923–931 (Dec. 1978).
Fine, D. H. & I. D. Mandel, "Indicators of Periodontal Disease Activity: An Evaluation," J. Clin. Periodontol, vol. 13, pp. 533–546 (month unknown 1986).
Guven, O. and J. G. A. M. De Visscher, "Salivary IgA in Periodontal Disease," J. Periodontology, vol. 53, No. 5, pp. 334–335 (May 1982).
Harper, D. S., I. B. Lamster & R. Celenti, "Relationship of Subgingival Plaque Flora to Lysosomal and Cytoplasmic Enzyme Activity in Gingival Crevicular Fluid,"J. Clin. Periodontol, vol. 16, pp. 164–169, (month unknown 1989).
Holmberg, K. and J. Killander, "Quantitative determination of immunoglobuline (IgG, IgA and IgM) and identification of IgA-type in the gingival fluid," J. Periodont. Res., vol. 6, No. 1, pp. 1–8 (month unknown 1971).
Iivanainen, M. and H. Savolainen, "Side Effects of Phenobarbital and Phenytoin During Long-term Treatment of Epilepsy," Acta Neurol. Scand., vol. 68, Suppl. 97, pp. 49–67 (month unknown 1983).
Kilian, M., B. Ellegaard & J. Mestecky, "Distribution of immunoglobulin isotypes including IgA subclasses in adult, juvenile, and rapidly progressive periodontitis," J. Clin. Periodontol, vol. 16, No. 3, pp. 179–184, (Mar. 1989).
Lamster, I. B., R. L. Oshrain, D. S. Harper, R. S. Celenti, C. A. Hovliaras & J. M. Gordon, "Enzyme Activity in Crevicular Fluid for Detection and Prediction of Clinical Attachment Loss in Patients with Chronic Adult Periodontitis," J. Periodontol., vol. 59, No. 8, pp. 516–523, (Aug. 1988).
Lamster, I. B., S. Wallenstein, S. Sengupta & T. Duffy, "Within-mouth Correlations For Indicators of the Host Response in Gingival Crevicular Fluid," Archs Oral Biol., vol. 35, No. 10, pp. 779–783 (month unknown 1990).

(List continued on next page.)

Primary Examiner—Carol E. Bidwell
Attorney, Agent, or Firm—Jean R. Crosmun; David L. Suter; Mick B. Graff

[57] ABSTRACT

The subject invention relates to methods and kits for detecting or evaluating risk of presently or later developing active periodontitis, comprising: (a) collecting gingival crevicular fluid; (b) measuring the amount in the gingival crevicular fluid of IgA; (c) measuring the amount in the gingival crevicular fluid of a marker for polymorphonuclear leukocytes; (d) comparing a ratio of the amounts obtained from steps (b) and (c) to a standard.

6 Claims, No Drawings

OTHER PUBLICATIONS

Landry, R. G., C. Mouton, L. Lamy, M. Deslauriers & J. F. Tessier, "Specific Sera IgA Titers as Realistic Indicator of Prognosis of Treatment," Journal of Dental Research, vol. 70, Special Issue, p. 319, Abstract No. 434, (Apr. 1991).

Lehner, T., "Immunological Aspects of Dental Caries and Periodontal Disease," Br. Med. Bull., vol. 31, No. 2, pp. 125–130 (May 1975).

Lindstrom, F. D. and L. E. A. Folke, "Salivary IgA in Periodontal Disease," Acta Odontol. Scand., vol. 31, No. 1, pp. 31–34 (month unknown 1973).

Orstavik, D. and P. Brandtzaeg, "Secretion of Parotid IgA in Relation To Gingival Inflammation and Dental Caries Experience in Man," Archs Oral. Biol., vol. 20, No. 11, pp. 701–704 (Nov. 1975).

Palcanis, K. G., I. K. Larjava, B. R. Wells, K. A. Suggs, J. R. Landis, D.E. Chadwick & M. K. Jeffcoat, "Elastase as an Indicator of Periiodontal Disease Progression," Journal of Periodontology, vol. 63, No. 4, pp. 237–242 (Apr. 1992).

PrognosStik TM Elastase Test System, sales brochure from Dentsply International, Inc., York, Pa., (Copyright 1990).

Saito, I., K. Komiyama, I. Moro, K. Akachi, N. Shiomi, K. Ito, S. Murai & S. Umemura, "Ultrastructural and Immunocytochemical Characterization of Polymorphonuclear Leukocytes from Gingival Crevice in Man," J. Periodontol., vol. 58, No. 7, pp. 493–497 (Jul. 1987).

Schonfeld, S. E., G. I. Drury & S. M. Herles, "Complement fixing activity in diseased human gingival tissues," Journal of Periodontal Research, vol. 16, No. 5, pp. 574–581 (Sep. 1981).

Sengupta, S., I. B. Lamster, A. Khocht, T. A. Duffy & J. M. Gordon, "The Effect of Treatment on IgG, IgA, and IgM and $\alpha$-2-macroglobulin in Gingival Crevicular Fluid From Patients With Chronic Adult Periodontitis," Archs Oral Biol., vol. 33, No. 6, pp. 425–431 (month unknown 1988).

Wilton, J. M. A., M. A. Curtis, I. R. Gillett, G. S. Griffiths, M. F. J. Maiden, J. A. C. Sterne, D. T. Wilson & N. W. Johnson, "Detection of high-risk groups and individuals for periodontal diseases: laboratory markers from analysis of saliva," J. Clin. Periodontol, vol. 16, No. 8, pp. 475–483 (Sep. 1989).

METHODS FOR EVALUATING RISK OF DEVELOPING PERIODONTITIS

TECHNICAL FIELD

The subject invention relates to improved methods for assessing the risk of experiencing active periodontitis by a patient or a periodontal site in the oral cavity.

BACKGROUND OF THE INVENTION

Plaque bacteria colonize the tooth and bring about an influx of bacterial toxins, enzymes, and metabolites which may prompt localized development of an inflammation of the gingival tissues, gingivitis. The local host tissue inflammatory response to the bacterial pathogens' challenge includes infiltration of a variety of cell types (e.g. polymorphonuclear leukocyte, lymphocytes, plasma cells, macrophages) that have various roles in counteracting the tissue insult presented by the plaque pathogens and their products. In many individuals, the continuing presence of plaque pathogens and the associated inflammatory response leads to periodontitis, which involves the progressive destruction of the connective tissue attachment for teeth and of alveolar bone supporting the teeth.

The periodontal attachment apparatus is comprised of the cementum, periodontal ligament and its component fibers connecting the tooth to the socket of alveolar bone. When healthy, the periodontal attachment occurs just apically of the junction between the tooth enamel and the cementum of the root. Clinically, loss of periodontal attachment at a specific site on a tooth is determined with a calibrated periodontal probe by measuring the distance between the junction of the root cementum and enamel and the level at the base of the periodontal pocket where a periodontal probe meets resistance to mechanical probing. If there is attachment loss, there likely is also a periodontal pocket. If loss continues due to periodontal pathogen colonization, alveolar bone loss may result. This tissue destruction may be retarded but is not reversed by traditional therapeutic interventions.

Within populations of patients having periodontitis, the rate of disease progression varies widely; additionally, within individual patients, the disease progresses at markedly different rates among different sites in the mouth. Individual teeth and their respective root surfaces in the mouth are each sites where periodontitis may occur with varying degrees of severity. Presently, it is believed that disease may progress in either a chronic linear fashion over time or in an episodic manner with bursts of disease activity separated by periods of remission. In either event, it is clear that when a patient population is followed over time there are marked differences in the incidence of clinically demonstrable disease progression among patients and among sites within each patient's mouth.

The prospective detection of patients and sites at increased risk of disease progression is very important to effective dental treatment. Detection of an increased risk for disease progression enables the early identification of those patients and those sites that most need therapeutic or preventative treatments to halt the tissue destructive phase of the disease process.

Presently, there are no effective means to evaluate a patient's risk, or a site's risk, of experiencing continued attachment loss, i.e. active disease. Clinical measures of disease progression provide a measure of prior disease activity but do not provide a means of differentiating among sites or patients with high or low levels of risk of future disease activity.

The host immune response to plaque pathogens includes producing both molecules that protect gingival tissues from the destructive effects of invading bacteria and also molecules produced during the host response that can destroy periodontal tissues. For example, lymphocytes produce antibodies against plaque pathogens that neutralize bacteria and their toxic products. Meanwhile, inflammatory cells can release various hydrolytic enzymes which can cleave and degrade protein and polysaccharides of key periodontal tissue structural components.

The antibodies produced against periodontal pathogens bind to the pathogens or their products forming antigen-antibody complexes. These antigen-antibody complexes result in the neutralization and agglutination of plaque pathogens and their products. The complexes also facilitate the phagocytosis, killing, and degradation of the pathogens and their products by the Polymorphonuclear leukocytes (PMNs). However, some of these antigen-antibody complexes can prompt secondary inflammatory responses because of their ability to activate the complement system, which is a cascade of proteolytic enzymes capable of activating various inflammatory mechanisms.

Betaglucuronidase (BG), which is a hydrolytic enzyme and an enzyme marker for PMN activation, is involved in the acid degradation of mucopolysaccharides/proteoglycans. Indeed, increased gingival crevicular fluid (GCF) levels of BG have been reported in periodontitis patients with an increased incidence of active periodontitis. Thus, it appears that with active periodontitis there is an increased engagement of periodontal pathogens by PMNs within or near the gingival tissues.

While bacterial pathogens are necessary for the development of gingivitis and periodontitis, measuring the presence or absence of specific bacterial pathogens themselves is not a sufficient or effective means of predicting the likelihood of experiencing active disease. Consequently, effort to develop a means of predicting future disease activity has been focused on the association of various molecules found in the gingival crevicular fluid exuded due to the host factor response during the course of the disease (see, Lamster, I. B., et al, Enzyme Activity in Crevicular Fluid for Detection and Prediction of Clinical Attachment Loss in Patients with Chronic Adult Peridontitis, *J. Periodontol.*, 59, pp. 516-523, (1988) (hereinafter Lamster), and Palcanis, K. G., et al, Elastase as an Indicator of Periodontal Disease Progression, *J. Periodontol.*, 63, pp. 237-242, (1992) (hereinafter Palcanis)).

The GCF comprises the same molecules as those produced by the host cells in the gingival tissues or gingival crevice. The GCF, therefore, provides a profile of those host molecules present in the gingival tissues and may be used to indicate the reactions and responses taking place therein. Current research tends to focus on measuring the presence of host molecules that might be associated with the destruction of gingival tissues. Thus, levels of various inflammatory mediators (e.g. Prostaglandins E2), putative tissue destructive/hydrolytic enzymes (e.g. Betaglucuronidase and elastase), and enzyme markers for cell death (e.g. aspartate aminotransferase) found in gingival crevicular fluid have been evaluated for their association with patients or sites having an increased risk of active disease as compared to those in which no measurable clinical change in periodontal attachment is detected (see, Lamster and Palcanis). The correlation between the presence of these molecules and future disease activity has not proved to be strong enough to provide a generally acceptable and reliable method of predicting risk of disease activity.

An object of the subject invention is to provide a method for detecting an increased risk for progression of periodontal disease in humans and lower animals.

A further object of the subject invention is to provide diagnostic kits useful for detecting and evaluating the risk of disease progression for patients or particular periodontal sites in humans or lower animals.

SUMMARY OF THE INVENTION

The subject invention relates to methods and kits for detecting or evaluating risk of presently or later developing active periodontitis, comprising: (a) collecting gingival crevicular fluid; (b) measuring the amount in the gingival crevicular fluid of IgA; (c) measuring the amount in the gingival crevicular fluid of a marker for polymorphonuclear leukocytes; (d) comparing a ratio of the amounts obtained from steps (b) and (c) to a standard.

DETAILED DESCRIPTION OF THE INVENTION

Diagnostic Methods

The subject invention relates to diagnostic methods for detecting patients or periodontal sites at risk of experiencing active periodontitis in humans or lower animals. These methods comprise measuring the levels of IgA and PMN marker in GCF, calculating a ratio of their values, and using that ratio to assess the risk of experiencing active periodontitis. Unexpectedly, the IgA/PMN-marker ratio appears to reflect the balance or imbalance of host response mechanisms that dictates the probability of active periodontitis occurrence. When the IgA/PMN-marker ratio for a patient or site is below the IgA/PMN-marker ratio found among patients or sites not at risk of active periodontitis, that patient or site is at increased risk of experiencing active periodontitis.

"Periodontal attachment", as used herein, means the connective tissue attachment which supports the tooth in the socket of alveolar bone.

The term "periodontitis", as used herein, means the tissue destructive disease involving the loss of periodontal attachment and/or the resorption of alveolar bone.

"Gingival tissue" as used herein, means the gum tissue and mucous membrane surrounding the tooth and alveolar attachment and bone.

"Gingival Crevice" as used herein, means that space lying between the inner aspect of the free gingiva and either the tooth enamel or the cementum, depending on the level of the periodontal attachment.

"Periodontal pocket" means an abnormally deep gingival crevice associated with periodontal disease, due to the migration of the gingival attachment towards the apex of the tooth root.

"Active periodontitis", as used herein, means that phase of periodontitis wherein a clinically detectable increase in connective tissue attachment loss and/or resorption of alveolar bone is occurring.

"Inactive periodontitis", as used herein, refers to disease for which no detectable increase in connective tissue attachment loss or resorption of alveolar bone is occurring.

"Gingival Crevicular Fluid" and "GCF" as used herein, mean that transudate of blood plasma collecting in the gingival crevice produced by leakage from capillaries in the free gingiva. "Gingivitis", as used herein, means inflammation of the gingival tissues.

"Disease", as used herein, means periodontitis.

"Site" as used herein, means specific locations (e.g. on the mesial, distal, buccal or lingual surfaces of a tooth root) around a tooth that are monitored for the presence of periodontitis.

"Marker" as used herein, means one or more specific molecules that can be detected and measured and indicate the presence of one or more mechanisms relevant to the disease pathology.

"IgA", as used herein, refers to serum-type immunoglobulin-A.

"PMN", as used herein, refers to polymorphonuclear leukocyte(s).

"GCF sample", as used herein, refers to an amount of GCF collected from the gingival crevice of a site or patient.

"GCF test sample", as used herein, refers to a GCF sample diluted into a standard volume of buffer from which aliquots are taken for subsequent analysis for GCF IgA or GCF PMN-marker.

"GCF IgA", as used herein, refers to the gingival crevicular fluid serum-type IgA detected in a GCF test sample. GCF IgA is inclusive of the IgA1 and IgA2 isotypes and is not restricted to IgA antibody specific for particular antigens.

"GCF BG", as used herein, refers to the amount of active Betaglucuronidase detected in a GCF test sample.

"GCF PMNs", as used herein, means the gingival crevicular polymorphonuclear leukocytes that migrate from the gingival tissues into the gingival crevice.

"PMN-marker", as used herein, refers to any one of a number of particular markers for active polymorphonuclear leukocytes.

"GCF PMN-marker", as used herein, refers to the PMN-marker detected in a GCF test sample.

"Activation of GCF PMNs", as used herein, means the process wherein the interaction of the GCF PMNs with bacteria in the gingival crevice, periodontal pocket or periodontal tissues leads to the elaboration of PMN metabolites, enzymes and/or byproducts.

The amount of correlation between risk of experiencing active disease and the IgA/PMN-marker ratio is dependent on the PMN-marker chosen. Some IgA/PMN-marker ratios are more reliable predictors than others. Suitable PMN-markers to be measured for purposes of the subject invention include those which represent the activation and degranulation of PMNs. These include but are not limited to Betaglucuronidase, the hydrolytic enzymes elastase, cathepsins (such as cathepsin B/L and cathepsin G), and gelatinase, the enzyme myeloperoxidase and metabolites that reflect early activation events of PMNs, such as leukotrienes (e.g. LTB4 or LTC4). Preferred PMN-markers are elastase and Betaglucuronidase.

The GCF IgA/PMN-marker ratio can be developed, among other methods, by dividing the total amount of GCF IgA present in a GCF sample by the total amount of the PMN-marker of interest present in the GCF sample; dividing the total amount of GCF IgA present in a standard aliquot of GCF test sample with the total amount of GCF PMN-marker present in a standard aliquot of GCF test sample; dividing the concentration of GCF IgA present in a GCF test sample by the concentration of GCF PMN-marker present in a GCF test sample; or by dividing the concentration of GCF IgA by the concentration of GCF PMN-marker.

There are various methods of collecting GCF. Such methods, include, among others, the method described in Lamster, Hartley & Vogel, Development of a Biochemical Profile for Gingival Crevicular Fluid, *J. Periodontology*, 56, (Suppl.) 13–21, (1985) (hereinafter Lamster II), incorporated herein by reference. By utilizing the above method of collection, a GCF sample may be obtained.

Methods to Measure GCF IgA

There are also various ways to measure the levels of IgA in samples of GCF. These include, but are not limited to, assays employing enzyme linked immunosorbent assays (ELISA), or radioimmunoassays (RIA) as detection systems.

Methods of taking a measurement of GCF IgA with an ELISA are described in Sengupta et al., The Effect of Treatment on IgG, IgA, IgM and alpha-2-Macroglobulin in Gingival Crevicular Fluid from Patients with Chronic Adult Periodontitis, *Arch. Oral Biol.*, 33, No. 6, pp. 425–431 (June, 1988) (hereinafter Sengupta), incorporated herein by reference. The method described therein and modifications of ELISA methods thereof employ a non-human, preferably non-primate, anti-human IgA "capture" antibody, which is a polyclonal or monoclonal anti-IgA antibody preparation. The capture antibody used is specific for IgA and does not cross react with human IgG, IgM, IgE, or IgD.

This anti-IgA "capture" antibody is typically cross-linked to either a solid support, such as a microtiter culture plate, or to a particulate matrix, such as latex. During incubation with the test sample this "capture" antibody captures the GCF IgA from either the test sample buffer into which the GCF has been dissolved or directly from the GCF sample itself and retains it upon the solid support/particulate matrix used in the immunoassay test of interest. The captured IgA may then be separated from the remainder of the GCF sample constituents, usually either by rinsing the surface to which the GCF IgA is complexed or by filtering the particulate complex to which the capture IgA is complexed. Subsequently, the captured antibody-GCF IgA complex is exposed to an antibody enzyme conjugate, such as peroxidase-conjugated rabbit IgG.

This antibody-enzyme conjugate employs an antibody that is specific for human IgA immunoglobulin and does not cross react with the anti-IgA capture antibody. This antibody typically is conjugated/linked either to a chromogenic enzyme, (e.g. horseradish peroxidase, alkaline phosphatase, B-galactosidase, or glucosidase) or to biotin. In the event that a biotinylated antibody is complexed with the captured IgA, there is a subsequent incubation with an anti-biotin antibody-enzyme conjugate (using, for example, one of the chromogenic enzymes noted above) or an avidin-chromogenic enzyme conjugate. The above capture-antibody-IgA-antibody-chromogenic enzyme complexes, may then be exposed to the chromogenic substrate appropriate for the respective conjugated enzymes (e.g. o-phenyldiamine dihydrochloride or p-nitrophosphate for HRP and alkaline phosphatase, respectively). The mixture is then incubated in an appropriate buffer to develop a color reaction, whose absorbance and/or intensity is proportional to the amount of IgA bound to the capture antibody (for background on ELISA methodology, see, Notermans, S. et al, The Enzyme-Linked Immunosorbent Assay (ELISA) for the Detection and Determination of Clostridium botulinum Toxins A, B, and E, *METHODS IN ENZYMOLOGY*, 84, pp. 223–238, (1984) (hereinafter Notermans); Butler, J. E., The Amplified ELISA: Principles of and Applications for the Comparative Quantitation of class and Subclass Antibodies and the Distribution of Antibodies and Antigens in Biochemical Separates, *METHODS IN ENZYMOLOGY*, 73, pp. 483–523 (1981) (hereinafter Butler); Sigma Immuno Chemicals Catalog 1992 (Sigma Chemical Company), (hereinafter Sigma); Engvall, E., et al, Enzyme-Linked Immunosorbent assay, ELISA, III. Quantitation of specific Antibodies by Enzyme-Labeled Anti-Immunoglobulin in Antigen-Coated Tubes, *J. OF IMMUNOL.*, 109, pp. 129–139, (1972) (hereinafter Engvall); Kato, K., et al, Enzyme-Linked Immunoassay: Conjugation of the FAB Fragment of Rabbit IgG with beta-Galactosidase from *E. coli* and Its Use for Immunoassay, *J. OF IMMUNOL.* 116, pp. 1554–1564, (1976) (hereinafter Kato); and Guesdon, J. L., Magnetic Solid Phase Enzyme Immunoassay for the Quantitation of Antigens and Antibodies: Application to Human Immunoglobin E, *METHODS IN ENZYMOLOGY*, 73, pp. 471–482, (1981), each incorporated herein by reference).

Suitable non-human "capture" antibodies include antiserum from mouse, rabbit, guinea pig, and goat (see Sengupta and Butler).

Suitable solid supports include polystyrene, filter paper, nitrocellulose, nylon, ferromagnetic spheres, and cyanogen bromide activated paper. Polystyrene and nitrocellulose are preferred (see, Butler; Pappas M. G., Recent Applications of the Dot-ELISA in Immunoparasitology, *VET. PARASITOLOGY*, 29, pp. 105–129, (1988); Lehtonen O. P., et al, Antigen attachment in ELISA, *J. IMMUNOL. METHODS*, 34, pp. 61–70, (1980); Smith, K. O., et al. Magnetic Transfer Devices for Use in Solid-Phase Radioimmunoassays and Enzyme-Linked Immunosorbent Assays, *J. INFECT. DIS.*, 136, pp. S329–336, (1977); Hendry, R. M., et al. Detection and Identification of Influenza Antigens by Nylon-Coupled Enzyme Linked Immuno Assay, *J. VIROL. METHODS*, 6, pp. 9–17, (1983) (hereinafter Hendry); Maiolini, R. et al, A Sandwich Method of Enzymoimmunoassay. I. Application to Rat and Human alpha-Fetoprotein, *J. IMMUNOL. METHODS*, 8, pp. 223–234, (1975), and Samanta A. K., et al., Enzyme Immunoassay of Testerone Using Nitrocellulose Discs as the Solid Phase, *J. CLIN. CHEM. BIOCHEM.* 28, pp. 943–947, (1990), each incorporated herein by reference).

Particulate matrices that may be used include polystyrene, latex, nylon, magnetic beads, glass, agarose and sepharose. Beaded polystyrene and latex are preferred (see, Nilsson B., A General Reagent for Amplifying ELISAs, *J. Immunol. Methods*, 114, pp. 89–93, (1988); Hendry; Gundersen, S. G., Magnetic Bead Antigen Capture, Enzyme-Linked Immunoassay in Microtitre Trays for Rapid Detection of Schistosomal Circulating Anodic Antigen, *J. Immunol. Methods*, 148, pp1–8, (1992); Oku, Y., Development of a Highly Sensitive Bead-ELISA to Detect Bacterial Protein Toxins, *Mi-*

*crobiol. Immunol.*, 32, pp. 807–816, (1988); and Harada, T., et al, Detection of Mucosal and Serum Antibodies Specific for the Capsular Polysaccharide of Haemophilus influenza Type B by Enzyme-Linked Immunosorbent Assay, *Microbiol. Immunol.* 29, pp. 591–600, (1985); and Sigma, each incorporated herein by reference).

Suitable antibody-enzyme conjugates and capture antibody pairs include mouse, goat, and rabbit anti-human-IgA antibodies of the IgG or IgM isotype conjugated to horseradish peroxidase (HRP), alkaline phosphatase, B-galactosidase, or glucosidase, alkaline pyrophosphatase, or urease (see Sigma; Notermans; Butler; Kato; Engvall; and Cerrone, M. C. et al, Description of a Urease-Based MicroELISA for the Analysis of Limiting Dilution Microcultures, *J. Immunol. Methods,* 138, pp. 65–75, (1991) (hereinafter Cerrone), incorporated herein by reference).

Suitable chromogenic substrates appropriate for use with conjugated HRP and alkaline phosphatase and urease include o-phenyldiamine dihydrochloride, p-nitrophosphate, and urea plus a pH indicator, respectively (see, Notermans; Butler; Cerrone; and Sigma).

Appropriate buffers for use in the subject invention include, among others, phosphate (0.001–0.1M) buffered (pH=6.6–7.4) saline solution (0.10–0.20N NaCl) with Tween (0.01%–0.1%), i.e. PBST. The preferred buffer is PBST, comprising 0.01M phosphate buffer at pH 7.01, in a 0.15N saline solution comprising 0.05% Tween.

ELISAs for use in the subject invention can also be conducted in solutions wherein visual color change reactions are used to reveal the level of IgA present. Such color change reactions may be conducted using chromogenic enzymes such as horse radish peroxidase, alkaline phosphatase, and urease and also can be coupled to fluorogenic substrates. (see, Notermans; Butler; Sigma; and Magnusson, K. E., et al, Fluorescence-Linked Immunosorbent Assay (FLISA) for Quantitation of Antibodies to Food Antigens, *Immunol. Invest.,* 16, pp. 227–240, (1987) incorporated herein by reference)

These color change assays can be quantitatively assessed by spectrophotometric means or through the use of visible assays. These assays may include the use of PBST solutions comprising one of the enzyme-antibody conjugates and their respective chromogenic substrates. The color change of these solutions can be compared to a chart composed of a series of color standards corresponding to the color change in the chromogenic substrates prompted by specific concentrations of IgA in the standard test samples. By matching the color change to the appropriate color standard the level of IgA in the test sample is determined.

The respective chromogenic substrates of the above mentioned antibody conjugates may include o-phenyldiamine dihydrochloride when horseradish peroxidase is used; p-nitrophosphate when alkaline phosphatase is used; and urea plus a pH indicator, when urease is used.

A series of color standards may be developed by conducting a series of colorimetric assays for standard test samples comprising a known range of IgA concentrations and then identifying color standards that match them for intensity and/or absorption. These color standards may then be arranged in the form of a chart which includes a range of color intensities/absorptions that correspond to a wide range of IgA concentrations likely to be found in test samples.

These immunoassays can be coupled to solid phase supports, beads, gels, other particulates or filters wherein the color change end products are captured on a solid phase support.

Suitable solid supports may include polystyrene, filter paper, and nitrocellulose. Polystyrene and nitrocellulose are preferred.

Particulate matrices that may be used include polystyrene, latex, nylon, magnetic beads, glass, agarose and sepharose. Beaded polystyrene and latex are preferred.

As with the solution assays, described above, a visual quantitative determination of the levels of GCF IgA is determined by comparison of the intensity of the colorimetric reaction for the GCF sample to the series of color standards representing the range of GCF IgA levels.

A series of color standards may be developed by conducting a series of colorimetric assays for standard test samples comprising a known range of IgA concentrations and then identifying color standards that match them for intensity and/or absorption. These color standards could then be arranged in the form of a chart which includes a range of color intensities or absorptions that correspond to a wide range of IgA concentrations likely to be found in test samples.

Another method of measuring the quantity of IgA in test samples derived from GCF is by Radio-immunoassay (RIA). An example of this method is described in Nerenberg and Prasad, *Methods in Enzymology,* 73, IMMUNOCHEMICAL TECHNIQUES Part B, pp. 666–691 (1981), incorporated herein by reference.

Methods to Measure GCF PMN-Marker

Markers for the presence of activated PMN's include Betaglucuronidase, the hydrolytic enzymes elastase, cathepsins (such as cathepsin G and cathepsin B/L), and gelatinase, the enzyme myeloperoxidase and metabolites that reflect early activation events of PMNs, such as leukotrienes (e.g. LTB4 or LTC4). Preferred PMN-markers are Beta-glucuronidase (BG) and elastase.

BG can be assayed by various methods, including but not limited to colorimetric and fluorometric methods.

Colorimetric methods of measuring BG are described in Lamster II. These colorimetric assays involve measuring the release of phenolphthalein from phenolphthalein glucuronic acid. These assays can be used to determine GCF BG levels both quantitatively, for example by spectrophotometric means, or through the use of visible assays.

GCF BG levels may be determined by spectrophotometric means by addition of an aliquot (50 μl) of the test sample to 100 μl of a solution of 0.075M acetate buffer at pH 4.5, 50 μl of 0.15M NaCl saline, and 50 μl of 0.03M phenolphthalein glucuronic acid at pH 4.5 and incubating at 56° C. for 2 hours. The reaction is terminated by adding 350 μl of 0.1M 2-amino-2-methyl-1-propanol buffer at pH 11. The absorbance at 550 nm is measured against a reagent blank and compared to a phenolphthalein standard curve. The results are used to calculate the level of BG present in each GCF test sample.

GCF BG levels may be determined by a visible assay through a modification of the spectrophotometric assay noted above. Specifically, the test sample may be analyzed as above until after the addition of the 2-amino-2-methyl-1-propanol buffer. At that time the visual color absorbance/intensity is compared to that of a color chart representing the absorbance/intensity range of the BG standard curve. Matching the test sample's visual color intensity/absorbance to the standard curve indicates the level of BG in the GCF test sample.

A further modification of the above test is to substitute the chromogenic substrate p-nitrophenyl-B-D-glucuronide for the phenolphthalein glucuronic acid. In this instance the release of yellow color following hydrolysis by BG can serve as a measure of the BG level in the test sample.

GCF BG also can be quantitated by means of fluorometric assays, as described in Pope, M. et al., *J. Dental Research*, 70, Abstract 704, April, 1991, incorporated herein by reference. Fluorometric assays involve the spectrophotometric/visual measurement of the release of a fluorescent by-product from a beta-glucuronic acid derivative of the fluorescent molecule. Fluorometric assays for BG have been developed for other applications. Such assays are described in Papasian et al, Rapid Identification of *Escherichia coli* with a Fluorogenic beta-D-Glucuronidase Assay, *DIAG. MICROBIOL. INFECT. DIS.*, 8 (4), pp. 255-8, (December, 1988) incorporated herein by reference. These techniques can be adapted to the detection of BG in GCF by the substitution of the fluorogenic precursor substrate 4-methylumbilliferyl-beta-D-glucuronide for phenolphthalein glucuronic acid, and then assessing the level of BG by the amount of fluorescent by-product, 4-methylumbilliferrone, liberated by BG when incubated as described in Lamster II. The level of fluorescent byproduct released is assessed by exposure of the assay to 360 nm UV light and comparing the intensity of fluorescence to that exhibited by a standard curve of fluorescence for various test samples comprising known concentrations of BG.

GCF BG levels can also be detected by use of an enzyme capture assays. Examples of such techniques are described in Holt et al, Enzyme Capture Assay for Rapid Detection of *Escherichia coli* in Oysters, *APPL. ENVIRON. MICROBIOL.*, 55, (1), pp. 229-32, (January, 1989), incorporated herein by reference. Application of this technique for detecting GCF BG in test samples is accomplished by preparing antibody preparations against human BG (as opposed to *E. coli* BG) and attaching the anti-human BG antibody preparation to a microtiter plate or other suitable surface. Subsequently, the test sample is added and incubated as described in Lamster II.

GCF elastase levels can be assayed by various methods including but not limited to colorimetric assays, ELISA, and fluorometric methods. Typically, these assays involve the release of chromogenic or fluorogenic compounds from derivatized peptides that are specifically hydrolyzed by elastase.

Colorimetric and fluorometric assays can be used to determine the levels of GCF elastase levels quantitatively, for example by spectrophotometric means and through visible assays.

Fluorometric assays involve the spectrophotometric/visual measurement of the release of a fluorescent by-product from a peptidyl derivative of the fluorescent molecule. Various fluorometric methods of measuring GCF elastase levels are described in Cox, S. W. and Eley B. M., Detection of Cathepsin B- and L-, Elastase-, Tryptase-, Trypsin-, and Dipeptidyl Peptidase IV-like Activities in Crevicular Fluid from Gingivitis and Periodontitis patients with Peptidyl Derivatives of 7-Amino-4-Trifluoromethyl Coumarin, *J. PERIO. RES.*, (24), 353-361, (1989) (hereinafter Cox I), and in Cox et al, A Simple, Combined Fluorogenic and Chromogenic Method for the Assay of Proteases in Gingival Crevicular Fluid, *J. PERIO. RES.*, (25), 164-171, (1990) (hereinafter Cox II), both incorporated herein by reference.

Suitable colorimetric methods of measuring PMN elastase levels in GCF samples are described in Cox II, Asman B., Peripheral PMN cells in Juvenile Periodontitis: Increased Release of Elastase and of Oxygen Radicals after Stimulation with Opsonized Bacteria., *J. CLIN. PERIODONTOL.*, (15), 360-364, (1988) (hereinafter Asman), and Kramer et al, Measurement of Free Human Leukocyte Elastase/alpha-1 Proteinase Inhibitor Complexes by an Enzyme-Linked Immunosorbent Assay, *J. IMMUNOLOGICAL METHODS*, (131), 41-48, (1990) (hereinafter Kramer), Suomalainen K., Characteristics of Neutral Proteases in Inflamed Human Gingiva, *SCAND. J. DENT. RES.*, (97), 346-354, (1989) (hereinafter Soumalainen), and in Palcanis, each incorporated herein by reference.

Determination of the GCF IgA/PMN-Marker Ratio

The GCF IgA/PMN-marker ratio can be calculated for either a patient or for a site. To determine the levels for an individual patient, the levels of GCF IgA and PMN-marker are determined for each GCF sample from each site of interest and the IgA/PMN-marker ratio for the GCF sample from each site is then determined. In turn, the mean value of IgA/PMN-marker ratios for the GCF samples from all the sites tested in a mouth can be calculated, yielding the IgA/PMN-marker ratio for a given patient.

The absolute value of the ratio of GCF IgA to PMN-marker is a function of the specific PMN-marker measured, detection systems used, and the units used to express the results. GCF IgA may be expressed as the mass of IgA present in the GCF (e.g. ng/sample), total number of ELISA units (e.g. absorbance units) per sample, RIA units per sample, or score on a standard scale for a visual ELISA assay. PMN-markers, for example, BG and elastase, can be expressed in enzyme units/sample, absorbance units for the spectrophotometric assay, fluorescence units, or as a score on a standard scale for a visual enzyme capture assay. Use of IgA ELISA units, such as absorbance units, per sample would give a different absolute value for the GCF IgA/BG ratio than would the use of nanograms of IgA per sample. Thus, for each embodiment of the subject invention the ratio must be calibrated to the specific values used to express levels of IgA/PMN-marker detected.

Calibration of the IgA/PMN-Marker Ratio

A standard against which the results of measuring the concentration of IgA and of PMN-marker may be compared may be determined through clinical testing. One method of deriving a standard is to evaluate populations of normal healthy patients and periodontitis patients longitudinally for the correlation of their respective IgA/PMN-marker ratios with subsequent changes in their clinical parameters. Given a specified means for quantitating GCF IgA and PMN-marker concentrations, the IgA/PMN-marker ratio: obtained from the populations may be used, allowing for statistical standard deviations, to categorize certain ratio ranges as representing low, moderate, or high risk of active periodontitis.

Groups of periodontally healthy patients (i.e. with no pockets greater than 4 mm in depth and no sites having greater than 2 mm loss of attachment) and groups of adult periodontitis patients may be enrolled in a study. Preferably, at least 10 patients are in each group; more preferably, at least 40 are in each group Samples of GCF are collected from a series of predetermined test sites in each patient, preferably from at least 2 sites per patient. More preferably samples are collected from at least 4 sites per patient. The levels of GCF IgA and PMN-marker are then determined through one or more specific assay methods as described above, or otherwise. Baseline clinical measurements, such as the periodontal attachment level or alveolar bone height, for each specified site in the mouth of each patient are then collected. The patients may then be given routine periodontal maintenance care, such as scaling and root planing, and are instructed to maintain their normal oral hygiene habits for a standard period of time, preferably from about 6 to about 12 weeks. Following that designated period of time all patients are recalled and their respective levels of periodontal attachment loss are determined. Patients and sites demonstrated to have meaningful levels of disease progression are designated as active disease patients/sites. Meaningful levels of disease progression may be evidenced by increased loss such as at least one site with greater than 2 mm of attachment loss and/or a demonstrable level of bone loss (i.e. loss that is greater than the statistical error of the measurement technique). To determine a standard against which to compare an individual patient's ratio value, the mean GCF IgA/PMN-marker ratios for the group of patients experiencing active disease and the group not experiencing active disease are then calculated. (Hereinafter these values are referred to as the "active group mean" and the "non-active group mean", respectively). To be a valid standard, the difference between the non-active group mean and the active group mean must be greater than the sum of their standard deviations. Also calculated, to determine a standard against which an individual site's ratio value may be compared, are the mean GCF IgA/PMN-marker ratios of sites experiencing active disease and sites not experiencing active disease (hereinafter these values are referred to as "active site mean" and "non-active site mean", respectively). To be a valid standard the difference between the non-active site mean and the active site mean must be greater than the sum of their standard deviations.

Thereafter, when using the same IgA and PMN-marker assay methods, any patient whose mean whole mouth IgA/PMN-marker ratio value is higher than one standard deviation below the non-active group mean is designated as a low risk patient. Similarly, patients whose IgA/PMN-marker ratio value is lower than one standard deviation above the active group mean is designated as a high risk patient. Those patients whose mean IgA/PMN-marker ratio value falls between one standard deviation above the active group mean and one standard deviation below the non-active group mean are designated as moderate risk patients.

Likewise, when using the same IgA and PMN-marker assay methods as those used to determine active and non-active site means, any site whose IgA/PMN-marker ratio value is higher than one standard deviation below the non-active site mean is designated as a low risk site and any site whose IgA/PMN-marker ratio value is lower than one standard deviation above the active site mean is designated as a high risk site. Those sites whose mean IgA/PMN-marker ratio value falls between one standard deviation above the active site mean and one standard deviation below the non-active site mean are designated as moderate risk sites.

Diagnostic Kits

The subject invention also relates to diagnostic products useful for detecting or evaluating the risk of presently or later developing active periodontitis in humans or lower animals. These diagnostic products comprise a means for measuring the amount of IgA and a means for measuring the amount of PMN-marker present in gingival crevicular fluid in one or more sites within the oral cavity of the human or lower animal being diagnosed.

An example of such a diagnostic product are diagnostic kits useful for detecting and evaluating the risk of disease progression for patients or sites in humans or lower animals.

A diagnostic kit used to determine the IgA/PMN-marker ratio for patients/sites comprises the materials necessary to assay the presence of IgA and a designated PMN-marker.

For a spectrophotometric ELISA analysis it will be necessary to include in the kit a means of collecting one or more GCF samples so that measurements of GCF levels of IgA and PMN-marker may be obtained. For this purpose, the kit may include pre-cut filter paper points, capillary tubes, capillary pipettes, micropipettes, reagents to flush the gingival crevice (for example, specific antibodies cross-linked to beads, gels or magnetic particles to harvest the IgA and BG from the gingival crevice).

For analyzing IgA, a kit may comprise containers, test tubes, culture tubes, reagent bottles, and microcentrifuge tubes containing buffered saline solutions which comprise the necessary reagents and/or in which the test samples are prepared and the assays are conducted to detect the presence of GCF IgA. Such components may include phosphate buffered saline Tween solutions comprising phosphate (0.001–0.1M) buffered to pH=6.6–7.4, NaCl (0.10–0.20N), and Tween (0.01–0.10%), i.e. PBST, and PBST solutions comprising necessary reagents and chromogenic substrates. Preferably, the PBST comprises 0.01M phosphate buffered (pH=7.01), saline (0.15N NaCl), with 0.05% Tween.

Diagnostic kits may also comprise incubation containers in which the assays are conducted. Suitable incubation containers may include test tubes, culture tubes, cuvettes, and microtiterplates. The preferred incubation containers are microtiterplates. More preferably the incubation containers are 96-well polystyrene microtiterplates, such as Nunc Immunoplate 1 (Roskilde, Denmark).

A diagnostic kit may also comprise a means to capture the IgA from the test sample and hold it to the bottom of the microtiter well during the development of the ELISA, such as an antiserum. Suitable antisera may include non-human, anti-human IgA "capture" antibody, such as a polyclonal or monoclonal anti-IgA antibody preparation, that is specific for IgA and does not cross react with human IgG, IgM, IgE, or IgD. Preferably the antiserum is from a non-primate, more preferably the antiserum is goat antihuman IgA. Still more preferred is goat IgG antihuman-IgA antiserum and a sodium carbonate/bicarbonate buffer, preferably 0.1M buffer at a pH of 9.6. Incubation of the capture antibody in the bicarbonate buffer in microtiter plates for 48 hours at 4° C. allows the attachment of the capture antibody to the bottom of the microtiter plate wells.

In a diagnostic kit, it may be necessary to include a derivatized antiserum to enable the detection of the IgA held by the capture antibody. Preferably the derivatized antiserum is of the same sort as the unlabelled antiserum, mentioned above. Suitable labels may include enzyme labeling, (such as with horseradish peroxidase, alkaline phosphatase, or urease), biotin labeling, radio labeling and fluorescence labeling. Preferred antisera is horseradish peroxidase-labeled goat IgG antihuman-IgA.

If the kit comprises a biotin labeled anti-IgA antiserum an avidin-label conjugate in PBST buffer should also be included. The avidin-label conjugate specifically binds to biotin and enables the detection of the biotin-labeled anti-IgA antiserum complexed with IgA and capture antibody. Suitable labels on avidin in the conjugate include enzyme labels (such as with horseradish peroxidase or alkaline phosphatase), radio labeling and fluorescence labeling. Preferred avidin-label conjugate is an avidin-enzyme conjugate, more preferred is avidin-horseradish peroxidase conjugate. To enable detection of the IgA-capture antibody-complex, via generation of a visible chromophore, a diagnostic kit may also comprise a buffer comprising a chromophore system. Suitable buffers include acetate and citrate buffers. Suitable chromophore systems include ortho-phenylenediamine, and p-nitrophosphate. If the buffer comprises ortho-phenylenediamine the buffer may also comprise from about 0.01% to about 1% percent hydrogen peroxide.

To maintain the pH in a range which is consistent with the optimal enzymatic function of the human PMN-marker, a diagnostic kit may comprise a buffer. Suitable buffers include buffers with a pKa within 0.5 pH units of pH 4.9, such as an acetate buffer. The preferred buffer is sodium acetate buffer. If acetate is used, the preferred concentration is from about 0.01M to about 0.5M. The preferred pH of the buffer is from about 4.5 to about 5.5. More preferably the pH is about 4.9.

A diagnostic kit may also comprise an anti-human betaglucuronidase antibody which may be linked to polystyrene, or other solid support, such as filter paper, nitrocellulose, gels, microcapsules, or beads. Preferably the antihuman BG antibody is bound to polystyrene and more preferably it is bound to a polystyrene microtiter plate.

To detect the presence of human BG a diagnostic kit may also comprise a chromogenic substrate for human BG. Such substrates include conjugates of beta-D-glucuronic acid, such as phenolphthalein-glucuronic acid, 4-nitrophenyl-beta-D-glucuronide, and 4-methylumbelliferyl-beta-D-glucuronide. The preferred substrate is phenolphthalein-glucuronic acid. If included, phenolphthalein-glucuronic acid is preferably provided in solution form at a pH of from about 4.5 to about 5.5.

A diagnostic kit may also comprise a saline solution with which to rinse the reagents from the ELISA plates between the incubation steps in the IgA ELISA assay. Suitable saline rinse solutions include phosphate buffered saline Tween solutions.

An HCl solution may be added to ELISA reactions to terminate them prior to taking an absorbance reading spectrophotometrically. Therefore, a kit may also comprise a solution of HCl to use in terminating an ELISA assay. The HCl is preferably in solution at a concentration of about 0.1M.

For the purpose of terminating the BG assay, it may be useful to include a buffer. Suitable buffers include amino alcohols, such as 2-amino-alcohols. The preferred buffer is 2-amino-2-methyl-1-propanol. Preferably, the buffer is in aqueous solution at a concentration of from about 0.01M to about 1M; more preferably the concentration is about 0.1M. The buffer is preferably at a pH of from about 9 to about 13; more preferably the buffer is at a pH of about 11.

It may be useful to include in a diagnostic kit, standard curves for the respective assays. Such standard curves may be used to convert the results of the respective IgA and PMN-marker assays, which are derived in units such as absorbance units and color intensity, into levels of IgA and PMN-marker in the test samples. Thus, the results in units of the respective assays (e.g. absorbance units or color intensity) may be expressed as a function of the level or concentration (e.g. mg/ml or $\mu g/\mu l$ of IgA or units/ml of PMN-marker activity). Standard curves may be developed by preparing standard test solutions representing the full range of IgA and PMN-marker concentrations in GCF, then assaying those standard solutions by conducting the respective IgA and PMN-marker colorimetric assays and plotting the results graphically. Such a graphic representation may be a plot of the respective absorbance values for the standard test solutions as a result of the respective assays versus the concentration of either IgA or PMN-marker represented by the levels added to the respective test samples.

Method and Diagnostic Kit Examples

The following non-limiting examples illustrate representative methods and diagnostic kits embodying the concepts of the subject invention.

EXAMPLE I

The following is a representative example of a method of the subject invention.

A spectrophotometric method for measuring risk of active disease comprises first collecting GCF samples at 16–20 sites per periodontitis patient. The collection is done as described in Lamster II.

A subsequent spectrophotometric analysis of the GCF IgA level is accomplished as described in Sengupta; the analysis of GCF BG is accomplished by methods described in Lamster II. The mean IgA/site (e.g. ng of IgA per 30 seconds of GCF collected) and mean BG/site (i.e. units of BG activity per 30 seconds of GCF collected) is then calculated. In turn, the mean IgA/BG ratio for each patient (i.e. for each subject (mean IgA/site)/(mean BG/site)) is calculated.

Thus, for example GCF is collected from a patient ("MG") as described above and that patient is determined to have a mean IgA/GCF sample/site of 45 ng and a mean BG/GCF sample/site of 2.3 Units. In turn, a mean IgA/BG ratio for patient MG is calculated to be 19.6.

Using the same above spectrophotometric methodology, a clinical study demonstrates that patients who experience active periodontitis have a mean IgA/BG ratio of 21.1±7.2; whereas, patients not experiencing any attachment loss have a mean IgA/BG ratio of 125.2±46.6.

Using the results of the clinical study as the standard and comparing MG's ratio results against that standard, the IgA/BG ratio of patient MG is less than one standard deviation above the mean of those subjects that experience active periodontitis. Therefore, MG is at high risk (>80% probability) of experiencing active periodontitis.

EXAMPLE II

The following is another representative example of a method of the subject invention and is a visual quantitative method for IgA and BG.

GCF is collected according to the methods of Lamster II; analysis of the GCF IgA is done according to the methods of Sengupta, with the exception that the chromogenic reaction is assessed by comparing the color change of the assay solution to a standard series of color intensities representing the range of GCF IgA concentrations.

The analysis of GCF BG is done according to the methods described in Lamster II with the exception that the levels of BG are assessed by comparing the color change of the assay solution to a series of color standards representing the color intensities of the BG chromogenic reaction for the range of GCF BG levels found in human GCF.

The color standards against which the color changes are compared are developed by performing IgA ELISA and BG enzyme assays for a series of test samples. Each test sample comprises a different known concentration of IgA and BG, and together the series represents a wide range of IgA and BG concentrations. The chromogenic color reactions for each respective sample is then matched to individual solutions comprising appropriate dyes to make a series of solutions of the same colors as the tested IgA and BG samples, thereby resulting in a series of colored solutions representing the different concentrations of IgA and BG. This series of solutions is a color intensity standard against which the results of chromogenic color reaction assays done on samples of GCF taken from a patient whose risk is to be evaluated may be compared.

The IgA/BG ratio is determined by matching the IgA and BG color intensities from the GCF samples assayed to according color standards on a matrix table whose Y-axis represents increasing concentrations of BG found in human GCF, and whose X-axis represents increasing concentrations of IgA. The point on the matrix table determined by the according values of the "X" and "Y" coordinates falls within an area determined to be of high, moderate, or low risk; the triangular area closer to the Y axis, representing a low IgA/BG ratio represents higher risk.

EXAMPLE III

The following is a representative example of a kit of the subject invention.

A spectrophotometric kit for the analysis of the IgA/BG is designed to be used with a microtiter plate reader and a spectrophotometer to read the results of the assays.

For the collection of GCF, the kit comprises 20 pre-cut filter paper strips.

For the analysis of GCF IgA, the kit comprises: 20 microcentrifuge tubes comprising PBST (0.01M phosphate buffered pH 7.01, saline 0.15N NaCl with 0.05% Tween); 50 ml of PBST rinse solution; 4 microtiterplates; 10 ml of goat antihuman IgA antiserum diluted 1:256,000 in a 0.1M carbonate/bicarbonate buffer at pH 9.6; 10 ml of peroxidase-labeled goat anti-human IgA, at a 1:4000 dilution in PBST buffer; 10 ml of a 0.1M citrate buffer comprising 30 mg percent ortho-phenylenediamine with 0.3 percent hydrogen peroxide; 10 ml of a 0.1M HCl solution, and a standard curve for the IgA assay.

For the BG assay, the kit comprises: 10 ml of a 0.075M acetate buffer at pH 4.9; 5 ml of a 0.03M solution of phenolphthalein glucuronic acid at pH 4.5; 5 ml of 0.15N NaCl saline solution; 50 ml of a 0.1M 2-amino-2-methyl-1-propanol buffer at pH 11; and a standard curve for the BG assay.

The kit additionally comprises a matrix table having the X-axis calibrated to represent increasing IgA levels, the Y-axis calibrated to represent increasing BG levels as found in human GCF, and having regions of the table marked wherein the respective IgA and BG co-ordinates define points within the marked regions to represent high, moderate and low risk categories.

EXAMPLE IV

The following is another representative example of a kit of the subject invention.

A spectrophotometric kit for the analysis of IgA/elastase ratio comprises:

For collection of GCF: 20 pre-cut filter paper strips.

For the analysis of GCF IgA: 20 microcentrifuge tubes comprising PBST (0.01M phosphate buffered pH 7.01, saline 0.15N NaCl with 0.05% Tween); 50 ml of PBST rinse solution; 4 microtiterplates; 10 ml of goat antihuman IgA antiserum diluted 1:256,000 in a 0.1M carbonate/bicarbonate buffer at pH 9.6; 10 ml of peroxidase-labeled goat anti-human IgA, at a 1:4000 dilution in PBST buffer; 10 ml of a 0.1M citrate buffer containing 30 mg percent ortho-phenylenediamine with 0.3 percent hydrogen peroxide; 10 ml of a 0.1M HCl solution, and a standard curve for the IgA assay.

For the elastase assay: 2 ml of a TST buffer (50 mM Tris HCl, pH 7.0, 0.15 NaCl and 1% Triton X-100: as described in Cox II), two white plastic trays, 40 6 mm diameter Whatman 3MM paper discs, which are impregnated with an elastase substrate (i.e. 250 $\mu$M of Methoxysuccinyl-Ala-Ala-Pro-Val-7-amino-4-trifluoromethylcourmari in 50 mM Tris HCl pH 9.0, and 350 mM NaCl and 5% Dimethylformamide and dried overnight), and 1 ml of 1% p-dimethylaminocinnamaldehyde in 1.0N HCl.

The chromogenic color reactions for the respective samples are then matched to solutions containing appropriate dyes to make a series of solutions of the same colors as the tested IgA and elastase samples, thereby resulting in a series of colored solutions representing the different concentrations of IgA and elastase. This series of solutions is a color intensity standard against which the results of chromogenic color reaction assays done on samples of GCF taken from a patient whose risk is to be measured may be compared.

The IgA/elastase ratio is determined by matching the IgA and elastase color intensities from the GCF samples assayed to according color standards on a matrix table whose Y-axis represents increasing concentrations of elastase found in human GCF, and whose X-axis represents increasing concentrations of IgA. The point on the matrix table determined by the coordinates falls within an area determined to be of high, moderate, or low risk; the area closer to the Y-axis is higher risk.

What is claimed is:

1. A method to aid in the evaluating risk of a periodontal site developing active periodontitis, comprising:
   (a) collecting gingival crevicular fluid (GCF) from the periodontal site;
   (b) measuring the amount of total IgA in the GCF;
   (c) measuring the amount of a polymorphonuclear leukocyte (PMN) marker in the GCF;
   (d) determining a ratio of total IgA/PMN marker for the periodontal site;
   (e) comparing the ratio of total IgA/PMN marker determined in step (d), to the ratio of total IgA/PMN marker of a non-active site standard and an active site standard, wherein
      (i) the non-active site standard is defined as a non-active site mean minus one standard deviation determined by performing steps (a), (b), (c) and (d) using gingival crevicular fluid obtained from sites in a group of subjects not having active periodontitis, and determining the mean (non-active site mean), and standard deviation thereof, of the ratios of total IgA/PMN marker obtained from performing step (d); and
      (ii) the active site standard is defined as an active site mean plus one standard deviation determined by performing steps (a), (b), (c) and (d) using gingival crevicular fluid obtained from sites having active periodontitis in a group of subjects, and determining the active site mean, and standard deviation thereof, of the ratios of total IgA/PMN marker obtained from performing step (d); and
      (iii) wherein the difference between the non-active site mean and the active site mean is greater than the sum of their standard deviations; and
   wherein the risk of developing active periodontitis is evaluated as (1) low, if the ratio of total IgA/PMN marker for the periodontal site is greater than the non-active site standard; (2) high, if the ratio of total IgA/PMN marker for the periodontal site is less than the active site standard; or (3) moderate, if the ratio of total IgA/PMN marker for the periodontal site is greater than the active site standard and less than the non-active site standard.

2. The method of claim 1, wherein the marker for polymorphonuclear leukocytes is Betaglucuronidase.

3. The method of claim 1, wherein the marker for polymorphonuclear leukocytes is elastase.

4. A method to aid in evaluating risk of a patient developing active periodontitis, comprising:
   (a) collecting gingival crevicular fluid (GCF) from a first periodontal site from the patient;
   (b) measuring the amount of total IgA in the GCF;
   (c) measuring the amount of a polymorphonuclear leukocyte (PMN) marker in the GCF;
   (d) determining a ratio of total IgA/PMN marker for the first periodontal site;
   (e) performing steps (a) through (d) on at least one or more additional periodontal sites;
   (f) obtaining the patient's personal mean ratio of total IgA/PMN marker by adding the ratio of total IgA/PMN marker for each periodontal site together and dividing by the total number of sites tested;
   (g) comparing the patient's personal mean ratio of total IgA/PMN marker determined in step (f), to the ratio of total IgA/PMN marker of a non-active group standard and an active group standard; wherein
      (i) the non-active group standard is defined as a non-active group mean minus one standard deviation determined by performing steps (a), (b), (c), (d), (e), and (f) using gingival crevicular fluid obtained from each member of a group of subjects not having active periodontitis, and determining the non-active group means, and standard deviation thereof, of the subjects' personal ratios of total IgA/PMN marker, obtained from performing step (f); and
      (ii) the active group standard is defined as an active group mean plus one standard deviation determined by performing steps (a), (b), (c), (d), (e), and (f) using gingival crevicular fluid obtained from each member of a group of subjects having active periodontitis, and determining the active group mean, the standard deviation thereof, of the subjects'personal ratios of total IgA/PMN marker obtained from performing step (f); and
      (iii) wherein the difference between the non-active group mean and the active group mean is greater than the sum of their standard deviations; and
   wherein the risk of developing active periodontitis is evaluated as (1) low, if the patient's personal ratio of total IgA/PMN marker is greater than the non-active group standard; (2) high, if the patient's personal ratio of total IgA/PMN marker is less than the active group standard; or (3) moderate, if the patient's personal ratio of total IgA/PMN marker is greater than the active site standard and less than the non-active site standard.

5. The method of claim 4, wherein the marker for polymorphonuclear leukocytes is Betaglucuronidase.

6. The method of claim 4, wherein the marker for polymorphonuclear leukocytes is elastase.

* * * * *